(12) United States Patent
Frisbee

(10) Patent No.: US 10,946,041 B2
(45) Date of Patent: Mar. 16, 2021

(54) METHODS, COMPOUNDS, AND SOLUTIONS FOR NEUROTRANSMITTER RESTORATION IN MAMMALS

(71) Applicant: Patrece Frisbee, Miami Beach, FL (US)

(72) Inventor: Patrece Frisbee, Miami Beach, FL (US)

( * ) Notice: Subject to any disclaimer, the term of this patent is extended or adjusted under 35 U.S.C. 154(b) by 253 days.

(21) Appl. No.: 15/936,559

(22) Filed: Mar. 27, 2018

(65) Prior Publication Data

US 2018/0271901 A1 Sep. 27, 2018

Related U.S. Application Data

(60) Provisional application No. 62/477,259, filed on Mar. 27, 2017.

(51) Int. Cl.

| | | |
|---|---|---|
| *A61K 33/10* | (2006.01) |
| *A61K 31/4415* | (2006.01) |
| *A61P 25/00* | (2006.01) |
| *A61K 9/00* | (2006.01) |
| *A61K 31/194* | (2006.01) |
| *A61K 36/41* | (2006.01) |
| *A61K 31/198* | (2006.01) |
| *A61K 36/185* | (2006.01) |

(52) U.S. Cl.
CPC ............ *A61K 33/10* (2013.01); *A61K 9/0095* (2013.01); *A61K 31/194* (2013.01); *A61K 31/198* (2013.01); *A61K 31/4415* (2013.01); *A61K 36/185* (2013.01); *A61K 36/41* (2013.01); *A61P 25/00* (2018.01)

(58) Field of Classification Search
None
See application file for complete search history.

(56) References Cited

U.S. PATENT DOCUMENTS

| | | | | |
|---|---|---|---|---|
| 2004/0204382 A1* | 10/2004 | Henderson | ........... | A61K 31/714 514/52 |
| 2011/0065662 A1* | 3/2011 | Rinsch | ................ | A61K 31/357 514/33 |
| 2016/0113987 A1* | 4/2016 | Choi | .................. | A61K 2300/00 424/439 |

OTHER PUBLICATIONS

Clifford, "The Potential Benefits of Red Beetroot Supplementation in Health and Disease", Nutrients, 2015, 7, 2801-2822 (Year: 2015).*
Herbach, "Betalain Stability and Degradation—Structural and Chromatic Aspects", Journal of Food Science, 71, 4, 2006, R41-R50 (Year: 2006).*

* cited by examiner

*Primary Examiner* — Robert T. Crow
*Assistant Examiner* — John P Nguyen
(74) *Attorney, Agent, or Firm* — Rogers Towers, P.A.; Joseph P. Kincart

(57) ABSTRACT

Methods, compounds, and solutions for neurotransmitter restoration in a mammalian brain. The compound comprises calcium carbonate, pyridoxine hydrochloric acid, magnesium citrate, zinc amino acid chelate, chromium amino acid chelate, and a mixture comprising L-Tryptophan, L-Glutamine, L-Tyrosine, DL-Phenylalanine, and *rhodiola*. A visual indicator may be included to provide a easily discernable indication of the efficacy of a mixed solution.

9 Claims, 6 Drawing Sheets

METHODS, COMPOUNDS, AND SOLUTIONS FOR NEUROTRANSMITTER RESTORATION IN MAMMALS

CROSS-REFERENCE TO RELATED APPLICATIONS

This application claims the benefit of U.S. Provisional Application Ser. No. 62/477,259, filed Mar. 27, 2017, entitled "METHODS, COMPOUNDS AND SOLUTIONS FOR NEUROTRANSMITTER REPLACEMENT IN MAMMALS" which is incorporated herein by reference in its entirety.

FIELD OF THE INVENTION

Embodiments of the present invention generally relate to neurotransmitters in a mammalian brain. In particular, the embodiments relate to compounds, methods, and solutions that restore neurotransmitters in the mammalian or a human brain.

BACKGROUND

Neurotransmitters are endogenous chemicals that relay information throughout the brain and body of an organism or a mammal, such as a human being. For example, the brain uses neurotransmitters to tell the heart to beat, lungs to breathe, and stomach to digest. Examples of major natural neurotransmitters include monoamines such as dopamine, norepinephrine and serotonin, amino acids such as Glutamate, Aspartate, D-serine, γ-aminobutyric Acid (GABA), peptides such as enkephalins, gastro transmitters, purines, and other chemicals. Neurotransmitters can also affect mood, sleep, concentration, weight, and cause adverse symptoms when they are out of balance. Therefore, optimal levels of neurotransmitters are required for appropriate body functions.

Neurotransmitter levels drop due to many different factors. For example, poor diet, stress, neurotoxins, genetic predisposition, drugs (prescription and recreational), alcohol and caffeine use, can drop these levels below an optimal range. Substance use, impulsive and compulsive disorders, and biochemical imbalances may also disrupt normal functioning of neurotransmitters in the brain. Further, suspension of the use of addictive substances may compromise neurotransmitter activity in a patient. The patient may experience abstinence symptoms that may persist even after the acute early symptoms of withdrawal subside. Further, abstinence without treatment may require several months or years for neurotransmitters to repair and rebalance.

For the foregoing reasons, there is a need for compounds and methods for restoration of neurotransmitters.

SUMMARY

Embodiments of the present invention provides a compound for restoring neurotransmitters in a mammalian brain. The compound includes calcium carbonate, pyridoxine hydrochloric acid, magnesium citrate, zinc amino acid chelate, chromium amino acid chelate, and a mixture containing L-Tryptophan, L-Glutamine, L-Tyrosine, DL-Phenylalanine, and rhodiola.

Embodiments of the present invention provides a method for restoring neurotransmitters in brain of a mammal. The method includes forming a powder formulation having calcium carbonate, pyridoxine hydrochloric acid, magnesium citrate, zinc amino acid chelate, chromium amino acid chelate, and a mixture containing L-Tryptophan, L-Glutamine, L-Tyrosine, DL-Phenylalanine, and rhodiola. The method further includes encapsulating the powder formulation in a capsule and preparing a solution by dissolving the capsule in a liquid. The solution may then be administered to the mammal for restoration of the neurotransmitters.

Embodiments of the present invention further provide a method for estimating an efficacy of a compound for restoring neurotransmitters in a mammalian brain. The method includes dissolving the compound in a liquid to prepare a solution, wherein the compound comprises calcium carbonate, pyridoxine hydrochloric acid, magnesium citrate, zinc amino acid chelate, chromium amino acid chelate, and a mixture containing L-Tryptophan, L-Glutamine, L-Tyrosine, DL-Phenylalanine, rhodiola, and a color change agent. The method further includes comparing a color of the solution to a color swatch to indicate the efficacy of the compound.

Embodiments of the present invention may provide a number of advantages. The compounds and methods of the present invention provide dietary and nutritional support factors for restoring neurotransmitters in a brain to reduce circulating cortisol levels, alleviate stress and anxiety, and reduce disease states associated with stress and anxiety.

These and other advantages will be apparent from the embodiments described herein.

The preceding is a simplified summary to provide an understanding of some embodiments of the present invention. This summary is neither an extensive nor exhaustive overview of the present invention and its various embodiments. The summary presents selected concepts of the embodiments of the present invention in a simplified form as an introduction to the more detailed description presented below. As will be appreciated, other embodiments of the present invention are possible utilizing, alone or in combination, one or more of the features set forth above or described in detail below.

BRIEF DESCRIPTION OF THE DRAWINGS

The foregoing and other aspects of the embodiments disclosed herein are best understood from the following detailed description when read in connection with the accompanying drawings. For the purpose of illustrating the embodiments disclosed herein, there is shown in the drawings embodiments that are presently preferred, it being understood, however, that the embodiments disclosed herein are not limited to the specific instrumentalities disclosed. Included in the drawings are the following figures.

Figure 1A:
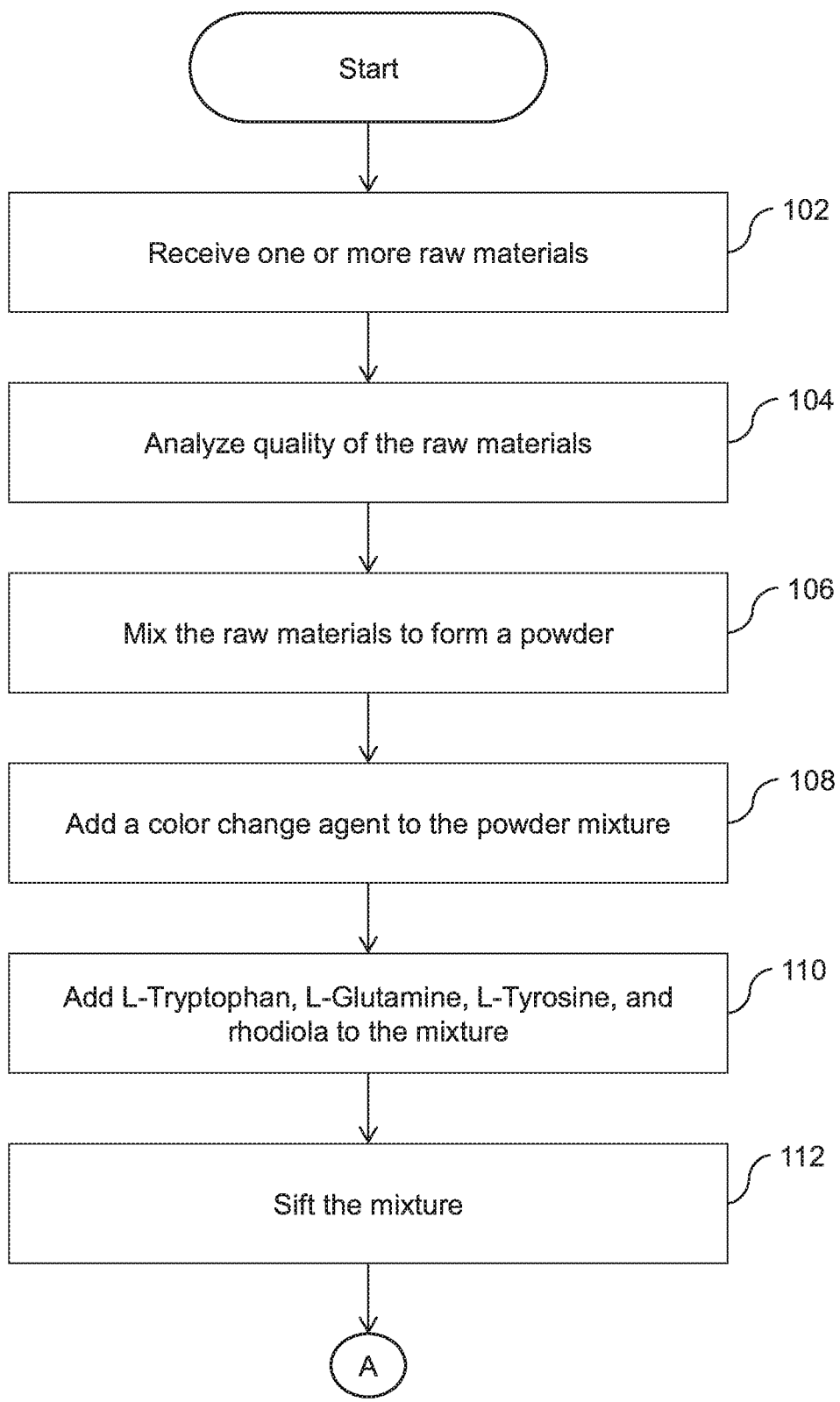
FIGS. 1A and 1B illustrate a method for restoring neurotransmitters in a brain of a mammal, in accordance with an embodiment of the present invention.

While embodiments of the present invention are described herein by way of example using several illustrative drawings, those skilled in the art will recognize the present invention is not limited to the embodiments or drawings described. It should be understood the drawings and the detailed description thereto are not intended to limit the present invention to the particular form disclosed, but to the contrary, the present invention is to cover all modifications, equivalents and alternatives falling within the spirit and scope of embodiments of the present invention as defined by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

Embodiments of the present invention will be described below in conjunction with exemplary compounds and methods for restoring neurotransmitters in a mammalian brain.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

In the following sections, detailed descriptions of examples and methods of the invention will be given. The description of both preferred and alternative examples though through are exemplary only, and it is understood that to those skilled in the art that variations, modifications, and alterations may be apparent. It is therefore to be understood that the examples do not limit the broadness of the aspects of the underlying invention as defined by the claims.

Optimal levels of neurotransmitters are generally required for appropriate body functions. Various brain functions and feeling can be attributed to neurotransmitters, for example, dopamine is associated with a reward, GABA with anxiety, norepinephrine with depression, enkephalins with cravings, and serotonin with sleep. Some of the causes of suboptimal levels of the neurotransmitters may be poor diet, stress, neurotoxins, genetic predisposition, drugs, alcohol, or caffeine use. Further, neurotransmitter imbalances may be linked to many diseases and disorders, including anxiety, memory loss, weight gain, mood disorders, addiction, depression, insomnia, eating disorders, Attention Deficit Hyperactivity Disorder (ADHD), Parkinson's, Tourette's, Autism, and compulsive and impulsive disorders.

Moreover, substance use or abuse problems may occur when biochemical imbalances disrupt the functioning of the neurotransmitters. For example, the imbalance may be caused by use of excessive addictive substances such as alcohol or drug. Stopping or withdrawal from the use of addictive substances may cause severe abstinence symptoms such as increased anxiety, depression, insomnia, mood swings, hypersensitivity to noise or lights, stress sensitivity, and cravings. These symptoms, also known as "chronic abstinence symptoms", persist even after the acute early symptoms of the withdrawal subside. Further, abstinence from an excessively used substance without a targeted treatment may require several months or years for neurotransmitter pathways to rebalance and repair. After the neurotransmitter pathways have rebalanced, a patient may have very low chances of relapsing. These positive results may be further improved or accelerated if a patient also follows a plan of health and wellness that includes regular sleep, good nutrition, and regular daily activity.

The present invention provides a compound for restoring or replacing neurotransmitters in a mammalian brain. In an embodiment of the invention, the compound includes calcium carbonate, pyridoxine hydrochloric acid, magnesium citrate, zinc amino acid chelate, chromium amino acid chelate, and a mixture comprising L-Tryptophan, L-Glutamine, L-Tyrosine, DL-Phenylalanine, and *rhodiola*.

In an embodiment of the invention, the compound includes approximately 6% of Calcium Carbonate, approximately 0.6% of Pyridoxine Hydrochloride (HCl), approximately 3% of Magnesium Citrate, approximately 1.2% Zinc Amino Acid Chelate, approximately 0.008% of Chromium Amino Acid Chelate, and approximately 89% of a mixture including L-Tryptophan, L-Glutamine, L-Tyrosine, DL-Phenylalanine and *Rhodiola*.

In an embodiment, the compound may rebuild and reboot the biochemistry of a patient's brain, which may result in the patient feeling more balanced, relaxed and calm, more at peace, and more in control. In another embodiment, the compound may be used to treat common abstinence symptoms such as anxiety, cravings, depression, insomnia, mood disorders, noise hypersensitivity, compulsive and impulsive disorders. The compound may further improve the quality of sleep, activate cognition, improve accuracy, alertness and attention, happiness, inner peace, weight wellness, and general wellbeing.

In an embodiment of the present invention, the compound targets neurotransmitters in the brain where anxiety, depression, and craving impulses originate. Therefore, the cravings associated with a substance withdrawal are reduced. In an embodiment of the present invention, the compound may reduce the cravings associated with the withdrawal symptoms within one week. In another embodiment, the compound may be used as a daily supplement to help maintain sobriety after initial detox treatment or for aiding in relapse prevention. The compound may also assist in rebuilding of damaged areas of the brain.

Description of Constituents in the Compound

L-Tryptophan (hereafter "tryptophan") is an essential amino acid that is not manufactured in a mammalian or human body. Tryptophan has been shown to combat stress, depression, insomnia, and also aid in weight control. Moreover, tryptophan may help relieve migraine headaches and alleviate some of the harmful effects of nicotine. Tryptophan may also help in the production of other neurotransmitters such as serotonin. Tryptophan may be administered as a food or a supplement.

L-Glutamine (hereafter "glutamine") is an amino acid found in a mammalian or human body like food for the brain (it can improve intelligence). Glutamine reduces fatigue, improves intelligence, and can help in treatment of various medical conditions such as, but not limited to, arthritis, connective tissue diseases, and fibromyalgia. Moreover, glutamine decreases cravings and stress in case of substance use disorder, and impulsive and compulsive disorders.

DL-Phenylalanine (hereafter "DLPA") is an amino acid that is not produced in the human body. DLPA is known to enhance sexual energy, improve memory and alertness, and support enhanced focus, attention, memory, motivation and mood. Further, DLPA alleviates symptoms of Pre-Menstrual Syndrome (PMS) and acts as an anti-depressant. Moreover, DLPA may assist the body in restoring other neurotransmitters, such as enkephalins, dopamine, and norepinephrine. Enkephalins aid in psychological pain relief, dopamine is linked to sensations of a pleasure, a reward, good feelings toward others, maternal and paternal love, and a norepinephrine is linked to arousal, and energy drive.

L-Tyrosine (hereafter "tyrosine") is an amino acid and generally used by cells to synthesize proteins. Tyrosine provides structural integrity to proteins, and aids in functioning of neurotransmitters and hormones (e.g., a thyroid hormone), mental functions, and a production of melanin. Tyrosine also assists in alleviating symptoms of drug and alcohol addiction, eating disorders, Parkinson's disease, emotional and environmental stress, lack of focus, poor attention and memory, lack of motivation and moodiness. Extremely low levels of tyrosine may cause muscle weakness, muscle loss, mood disorders, low protein levels, and liver damage.

Calcium is a common mineral that is essential for bones, teeth, soft tissues, intracellular fluids and blood. Optimal amount of calcium in the body is useful in easing insomnia, regulating heartbeat, and in providing emotional stability. Calcium deficiency is common in drug and alcohol addicts, due to poor diet and therefore, inadequate intake of calcium. In some cases, calcium deficiency may be caused due to use of sugar, caffeine, nicotine, alcohol, and other drugs, which may cause the body to eliminate calcium. For example, caffeine increases the urinary excretion of calcium, resulting in lower calcium levels. Calcium deficiency may cause lack of rational emotion, feelings of irritability, sudden unexplained tears, or sleep problems. Calcium may be one of the most important nutrient for a recovering addict. In an embodiment of the present invention, calcium may be incorporated in the compound as calcium citrate.

Magnesium is an essential mineral that makes up about 0.05% of human body weight. Magnesium activates enzymes necessary for the metabolism of carbohydrates and amino acids and helps in regulating acid-alkaline balance in the body. Further, magnesium may help in promoting absorption and metabolism of other minerals such as calcium, phosphorus, sodium, and potassium. Magnesium also helps the body in utilizing B complex, and vitamins C and E. Magnesium contributes to bone growth, proper functioning of the heart and other muscles, and like calcium, support a strong and calm nervous system. Consumption of high levels of sugar, caffeine, alcohol, and drugs may cause magnesium deficiency. Low calcium and magnesium levels are major contributing factors in cases of irritability, pain, and muscular/nervous system disorders that alcoholics and addicts experience during the withdrawal and recovery phases. In an embodiment of the present invention, the compound enables replenishment of calcium and magnesium in the body. In an embodiment of the present invention, magnesium may be incorporated in the compound as magnesium citrate.

Vitamin B6 (hereafter "B-vitamin") is necessary for the nervous system of the body to function normally. B-vitamin assists in creation of neurotransmitters such as GABA, enkephalins, dopamine and norepinephrine, by helping amino acids cross the blood-brain barrier. Consumption of excessive amounts of sugar, caffeine, alcohol, and drugs often causes B-vitamin deficiencies. Moreover, patients recovering from drug and alcohol addiction may have B-vitamin deficiency. In some cases, the deficiency may be present before the addiction, as B-vitamin deficiency may itself cause cravings for addictive substances. Therefore, B-vitamin is constructive during recovery from substance abuse. Further, use of B-vitamin may eliminate or diminish withdrawal symptoms, help eliminate cravings, boost mental outlook and stability, and aid the regeneration of the liver, endocrine glands, and nervous system. In an embodiment of the present invention, B-vitamin may be incorporated in the compound as Pyridoxal-5-Phosphate. In another embodiment of the present invention, B-vitamin may be incorporated in the compound as Pyridoxine Hydrochloric Acid (HCl).

Zinc is an essential mineral for various body and enzyme functions. Further, zinc may assist in liver function, brain function, insulin function, digestion, providing healthy immune system. Nutritional imbalance including consumption of too much sugar, caffeine, alcohol, and drugs can reduce levels of zinc stored in a person's liver. Zinc deficiency may cause cold extremities, poor peripheral circulation, loss of taste and smell, poor wound healing, lethargy, poor appetite, acne, and hypothyroidism. In an embodiment of the present invention, zinc may be incorporated in the compound as zinc amino acid chelate.

Chromium is a mineral that helps in regulating blood sugar or glucose in the body. Chromium may be especially important in people suffering from addiction. Deficiency of chromium may cause hypoglycemia, diabetes, and heart disease. In an embodiment of the present invention, chromium may be incorporated in the compound as chromium amino acid chelate.

*Rhodiola* is a herb that includes several active materials such as polyphenols and phytochemicals. *Rhodiola* may be used to reduce stress, alleviate fatigue, boost mental performance, and improve physical and mental fitness, and resilience. Further, *rhodiola* may be used to reduce mild to moderate depression. When combined with tricyclic antidepressants, *rhodiola* use has shown to ease antidepressant side effects, particularly fatigue and sexual dysfunction. Moreover, *rhodiola* may be beneficial in chronic fatigue and fibromyalgia syndromes, and treatment of ADHD, since it activates cognition and improves accuracy, alertness, and attention. In an embodiment of the present invention, *Rhodiola rosea* or root may be incorporated in the compound.

The compound may include additives for sweetening. In an embodiment of the present invention, the additives may include naturally occurring, zero-calorie sweeteners, for example, xylitol or *stevia*. In some examples, the formulation is flavored with natural fruit punch flavor. The compound may further include citric acid, sea salt, natural flavors, and natural coloring.

In an embodiment of the invention, the compound may in the form of a powder formulation. The powder formulation can be dissolved in a liquid, such as purified water to prepare a solution for ingestion by a person. The powder formulation enables efficient absorption of the compound in a body. In another embodiment, the compound may be in a form of granules. In an embodiment, the compound may be encapsulated in a capsule.

The compound may include a color change agent (also referred to as a visual indicator) such as beet root powder, in an embodiment of the present invention. The color change agent provides a visual indication of efficacy of a mixed solution. The beet powder provides a color to the solution that is prepared by dissolving the compound in a liquid. The color change agent may interact with one or more other constituents of the compound to provide a color to the solution. The color of the solution will change color based upon an amount of time that the powder is placed into solution. For example, a visual indicator or color change agent that includes beet powder darkens over time after being placed in solution. A darkened color may correspond to an amount of time in which it takes the powder placed in solution to lose some attribute that is beneficial to a person that imbibes the solution. Accordingly, the darkened solution will have less efficacy than a light solution.

The change in color is not the reason for the decreased efficacy, but the time in solution that transpired in order to darken the beet powder is indicative of a loss of efficacy. For example, beet powder will oxidize when placed in solution. Other visual indicators may also oxidize and change their color. Accordingly, other vegetables or fruits may be powdered and used a visual indicators. Other change agents of visual indicators may include a colorant that is encapsulated by a coating wherein the coating dissolves in solution. As the coating dissolves, the colorant is released into the solution and changes the color of the solution. A variety of mechanisms for color change may therefore be used to indicate a diminished efficacy of the change in the solution.

In some embodiments, a change in color is due to oxidation of beet root powder. In another embodiment, the change in color is caused by exposure or interaction of the beet root powder with other constituents such as amino acids. The color of the solution can therefore be compared to color swatch to estimate the efficacy and freshness of the solution. In an embodiment of the invention, the hue of the solution may change over time to indicate the efficacy of the solution.

Figure 1B:
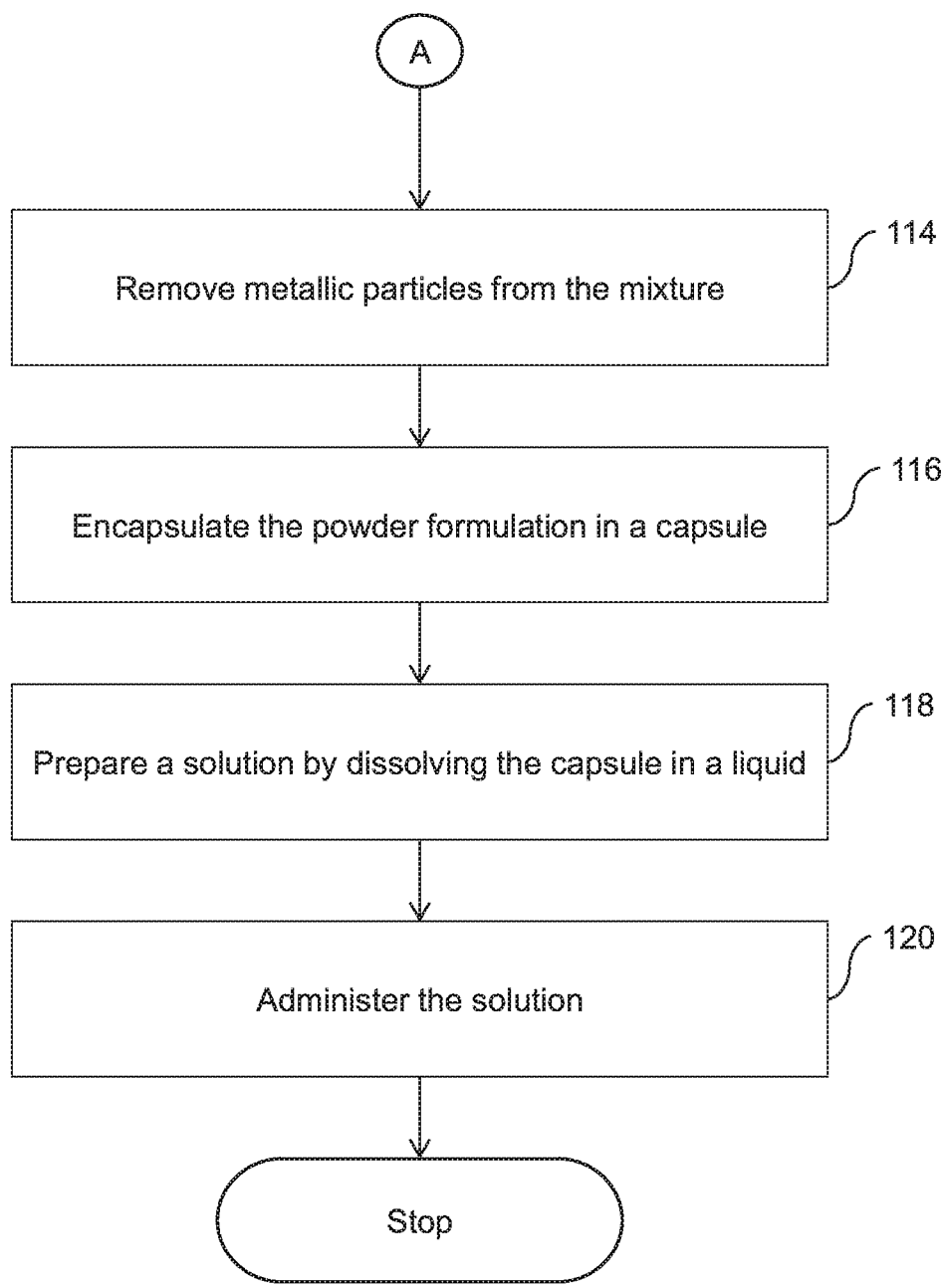

FIGS. 1A and 1B illustrate a method for restoring neurotransmitters in a brain of a mammal, in accordance with an embodiment of the present invention. The neurotransmitters may be restored by administering a compound. At step 102, raw materials required to prepare the compound are received. In an embodiment of the present invention, the raw materials may include, but not limited to, calcium carbonate, pyridoxine hydrochloric acid, magnesium citrate, zinc amino acid chelate, chromium amino acid chelate. Thereafter, at step 104, the quality of the raw materials is analyzed. In an embodiment of the present invention, the raw materials are analyzed through several tests, including but not limited to, microbiological, identification, organoleptic evaluation, loss on drying, pH, specific gravity, and other such tests or assays.

At step 106, the raw materials are mixed to form a powder formulation. In an embodiment of the present invention, the raw materials are mixed to form a coarse powder containing granules. Thereafter, at step 108, a color change agent is added to the mixture. The color change agent is beet root powder, in an embodiment of the present invention.

At step 110, amino acids such as L-Tryptophan, L-Glutamine, L-Tyrosine are added to the mixture. In an embodiment of the present invention, the amino acids may be neurotransmitter precursors. Further, *rhodiola* is added to the mixture at step 110. As discussed above, *rhodiola* is an herb that includes several active materials such as polyphenols and phytochemicals. *Rhodiola* may be used to reduce stress, alleviate fatigue, boost mental performance, and improve physical and mental fitness, and resilience. The powder may further include natural sweeteners, citric acid, sea salt, natural flavors, and natural coloring, in an embodiment of the present invention. Thereafter, at step 112, the mixture is sifted. The mixture is sifted to achieve an appropriate particle or granule size for the powder. In an embodiment of the present invention, sifting may be performed multiple times to achieve the appropriate size for the powder.

The various mixing and sifting processes as well as the initial raw material processing may inadvertently add pieces of metals from the various processing equipment. At step 114, the powder is checked for any magnetic particles, and subsequently the magnetic particles are removed from the powder formulation. In an embodiment of the present invention, the magnetic particles are removed by using magnetic attraction. Thereafter, at step 116, the powder formulation is encapsulated in capsules. The capsules may be gelatin capsules, in an embodiment of the present invention. The capsules are dissolvable in liquids, for example, water.

At step 118, a solution is prepared by dissolving the capsule in a liquid. In an embodiment of the present invention, the capsule is dissolved in purified water in a predefined dosage. The predefined dosage may depend on the age, weight, gender, and other physical and mental attributes of an intended patient. Subsequently, the solution is administered to the patient, at step 120. The patient may ingest the compound by drinking the solution. In an embodiment of the present invention, the color of the solution may be compared to a color swatch to estimate an efficacy of the solution.

The compound disclosed in the present invention assists in a healthy lifestyle. Moreover, several essential vitamins, minerals, trace minerals, and nutrient derivatives, in the compound may eliminate or reduce the severity of artificial chemical craving symptoms. In an embodiment of the present invention, the severity of artificial chemical craving symptoms may be reduced within weeks or, in some cases, days.

Figure 2A:
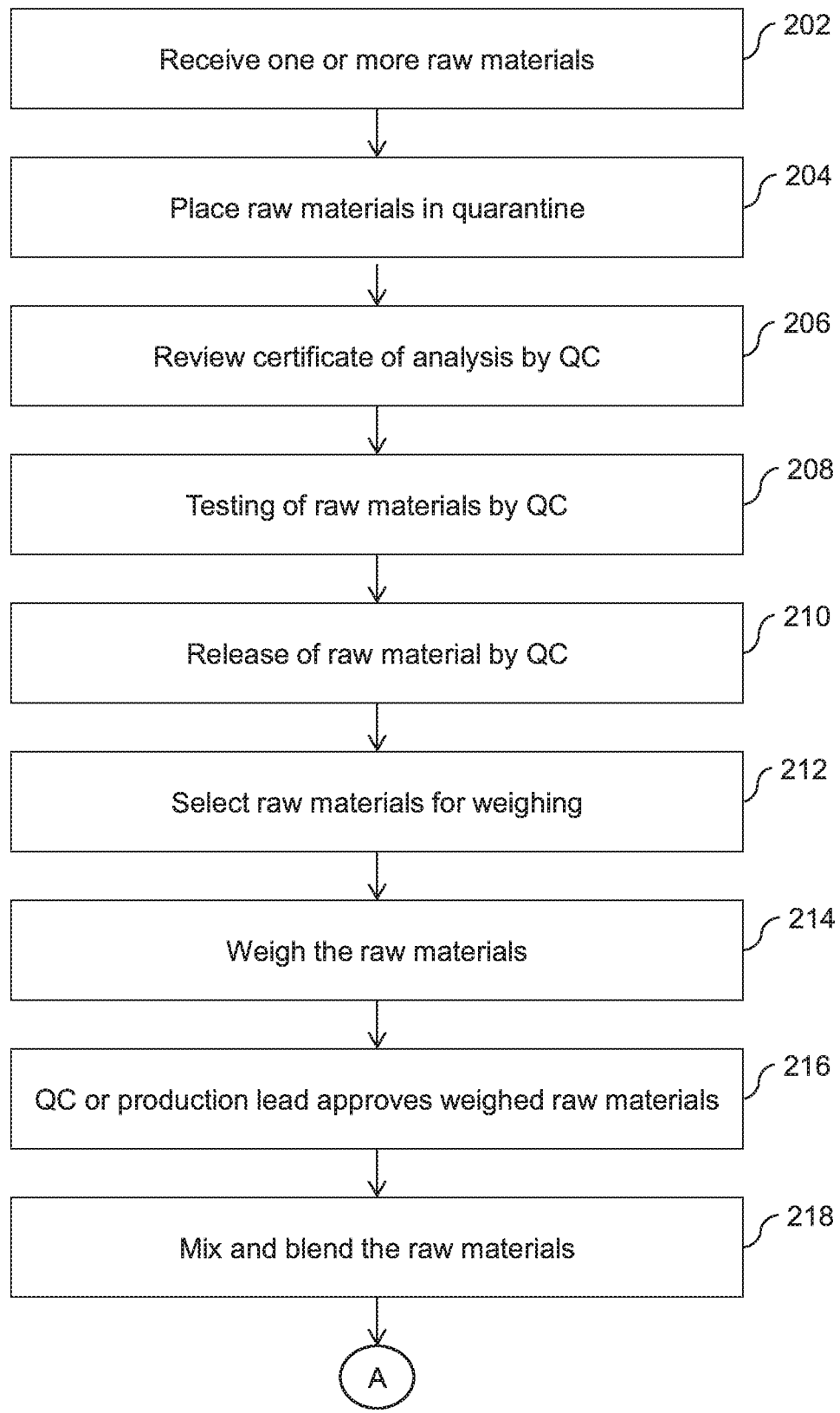
FIGS. 2A-2B illustrate a process flow for preparing a compound for restoring neurotransmitters in a brain of a mammal, in accordance with an embodiment of the present invention.
Figure 2B:
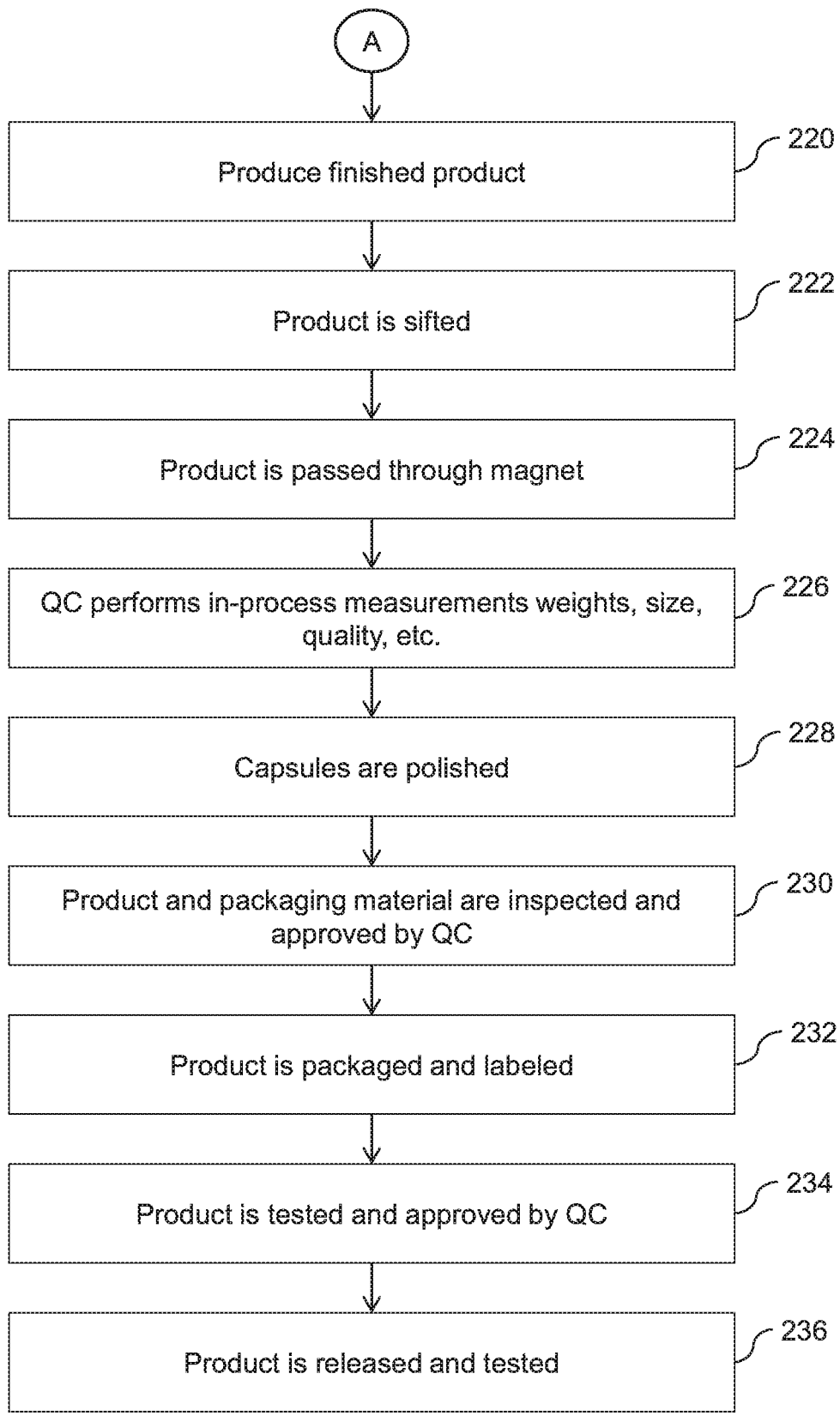

FIGS. 2A-2B illustrate a process flow for preparing a compound for restoring neurotransmitters in a brain of a mammal, in accordance with an embodiment of the present invention. The process may be useful in preparing the compound having high quality and effectiveness. At step 202, raw materials for the compound are received. Further, unique lot numbers are assigned to the raw materials for tracking them through the process. Thereafter, at step 204, the raw materials are placed into quarantine until tests may be performed upon them. At step 206, certificates of analysis of the raw materials are reviewed by a quality control. Subsequently, at step 208, the raw materials may be tested by the quality control. In an embodiment of the present invention, the testing may include, but not limited to, microbiological, identification, organoleptic evaluation, loss on drying, pH, specific gravity, and other such tests or assays. Thereafter, at step 210, the raw materials may be released by the quality control, based on satisfactory test results.

At step 212, the raw materials may be selected for weighing. For example, the raw materials may be selected from a warehouse for weighing. Thereafter, at step 214, the raw materials may be weighed. Subsequently, the quality control or a production lead may approve the weighed raw materials for production purposes, at step 216.

Further, at step 218, the raw materials are mixed and blended. Thereafter, at step 220, a finished product is produced. In an embodiment of the present invention, the finished product is a powder formulation. At step 222, the product is sifted. The sifting may produce the product with a predefined particle size range. In an embodiment of the present invention, multiple sifting processes may be required to achieve the predefined particle size range of the granule for the powder.

The various mixing and sifting processes as well as the initial raw material processing may inadvertently add pieces of metals from the various processing equipment. At step 224, the product is passed through magnets to check for any magnetic particles, and subsequently the magnetic particles are removed from the powder. Thereafter, at step 226, the product may be analyzed by the quality control by performing various quality tests. For example, the quality tests may include, but not limited to, weight, density, particle sizing, contaminant sensing, quality, and the like.

At step 228, the product is filled or encapsulated in capsules, and the capsules are polished. At step 230, the quality control inspects and approves the product and its packaging materials. Subsequently, at step 232, the product may be packaged and labeled. The labeled product is subjected to an additional quality control check, at step 234. The additional quality control check may enable confirmation of quality of the powder product and any packaging, gel capsules, and other constituents that may be used as part of a final product. Thereafter, at step 236, the final product may be released after satisfactory quality check results. In an embodiment of the present invention, random sample testing may be performed on the final product.

Figure 3:
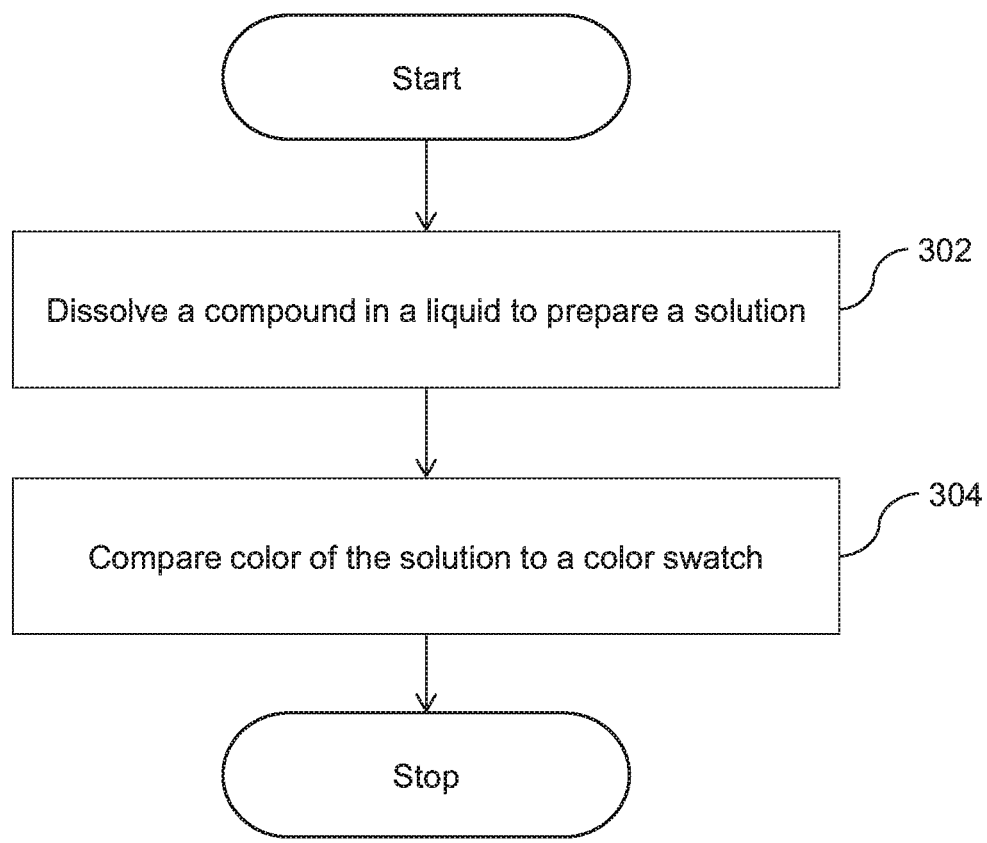
FIG. 3 illustrate a method for estimating an efficacy of a compound for restoring neurotransmitters in a mammalian brain, in accordance with an embodiment of the present invention.

FIG. 3 illustrate a method for estimating an efficacy of a compound for restoring neurotransmitters in a mammalian brain, in accordance with an embodiment of the present invention. As discussed above, an efficacy of the solution formed by dissolving the compound in a liquid may diminish over a time. At step 302, the solution is prepared by dissolving a capsule in a liquid. In an embodiment of the present invention, the capsule includes the compound and is dissolved in a purified water in a predefined dosage. The predefined dosage may depend on the age, weight, gender, and other physical and mental attributes of an intended patient. A color change agent in the compound may provide a pink type color to the solution, in an embodiment of the present invention. The color change agent may interact or react chemically with one or more other constituents, raw materials, or a color change agent, or additives of the compound to provide a color to the solution. In an embodiment, the change in color is due to oxidation of beet root powder. In another embodiment, the change in color is caused by exposure or interaction of the beet root powder with other constituents such as the amino acids.

Thereafter, at step 304, the color of the solution is compared to color swatch to estimate the efficacy and freshness of the solution. In an embodiment of the present invention, the efficacy may be diminished over a time. For example, the efficacy may be significantly diminished over a time, such as but not limited to, thirty minutes from preparation of the solution. In an embodiment of the present invention, the color of the solution may darken with time. In another embodiment of the present invention, one or both of a color and a hue of the solution changes over time. For example, the color of the solution may change from pink to a darker purple, or even black after a time from the preparation of the solution. In an embodiment of the present invention, only the efficacy of the amino acids is diminished over the time.

Figure 4:
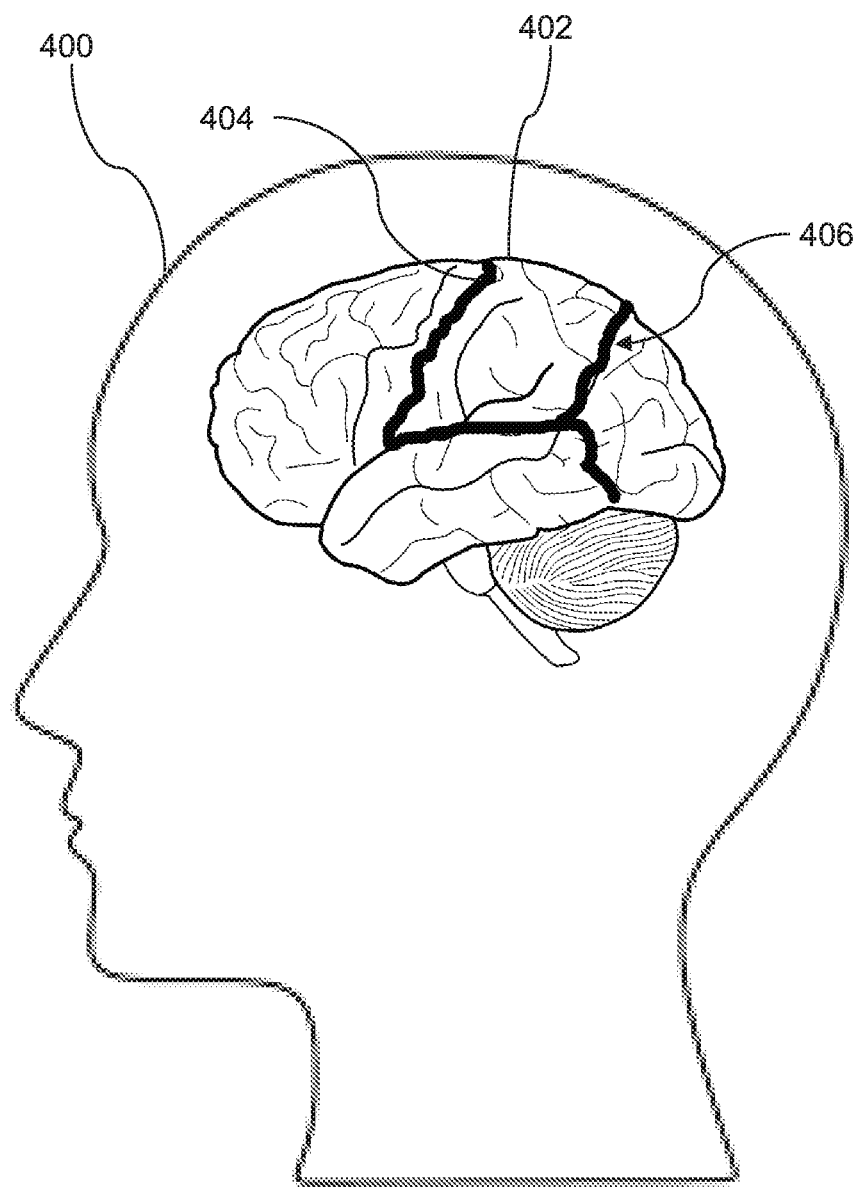
FIG. 4 illustrates an exemplary diagram of a human head and a brain.

FIG. 4 illustrates an exemplary diagram of a human head 400 and a brain 402. As discussed above, the compound may be assist in restoration of neurotransmitters in the human brain. The brain 402 may include vascular structures 404 that may transport the solution after ingestion into blood streams of a patient. The solution may then be transferred from the vascular structures 404 to brain tissues 406. In the brain tissues 406, the constituents of the compound may support the restoration and creation of new neurotransmitters.

A number of embodiments of the present invention have been described. While this specification contains many specific implementation details, there should not be construed as limitations on the scope of any inventions or of what may be claimed, but rather as descriptions of features specific to particular embodiments of the present invention. While embodiments of the present invention are described herein by way of example using several illustrative drawings, those skilled in the art will recognize the present invention is not limited to the embodiments or drawings described. It should be understood, the drawings and the detailed description thereto are not intended to limit the present invention to the form disclosed, but to the contrary, the present invention is to cover all modification, equivalents and alternatives falling within the spirit and scope of embodiments of the present invention as defined by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Certain features that are described in this specification in the context of separate embodiments can also be implemented in combination in a single embodiment. Conversely, various features that are described in the context of a single embodiment can also be implemented in combination in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while method steps may be depicted in the drawings in a particular order, this should not be understood as requiring that such operations be performed in the particular order shown or in a sequential order, or that all illustrated operations be performed, to achieve desirable results.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. Nevertheless, it will be understood that various modifications may be made without departing from the spirit and scope of the claimed invention.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

A number of variations and modifications of the present invention can be used. It would be possible to provide for some features of the present invention without providing others.

The foregoing discussion of the present invention has been presented for purposes of illustration and description. It is not intended to limit the present invention to the form or forms disclosed herein. In the foregoing Detailed Description, for example, various features of the present invention are grouped together in one or more embodiments, configurations, or aspects for the purpose of streamlining the present invention. The features of the embodiments, configurations, or aspects may be combined in alternate embodiments, configurations, or aspects other than those discussed above.

This method of present invention is not to be interpreted as reflecting an intention the present invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate embodiment of the present invention.

Moreover, though the description of the present invention has included description of one or more embodiments, configurations, or aspects and certain variations and modifications, other variations, combinations, and modifications are within the scope of the present invention, e.g., as may be within the skill and knowledge of those in the art, after understanding the present invention. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for informing a patient of an efficacy of a dissolved composition in the form of a powder formulation mixture of constituents for restoring neurotransmitters in a mammalian brain, the method comprising:
    dissolving the mixture of constituents in a liquid to prepare a solution, wherein the constituents comprises calcium carbonate, pyridoxine hydrochloric acid, magnesium citrate, zinc amino acid chelate, chromium amino acid chelate, and a mixture comprising L-Tryptophan, L-Glutamine, L-Tyrosine, DL-Phenylalanine, *rhodiola*, and a color change agent comprising beet root powder, wherein the dissolving causes the color change agent to interact with one or more constituents to provide an initial color of the solution;
    changing the color of the solution based upon an elapsed period amount of time the constituents are placed in solution;
    with the changing of color of the solution, indicating to an observer a loss of an attribute beneficial to efficacy of the solution for restoring neurotransmitters to the brain with the elapsed period amount of time the constituents are placed in solution;
    comparing a color of the solution to a color swatch; and
    indicating an efficacy of the solution for restoring neurotransmitters to the brain based upon the comparing of the color of the solution to the color of the swatch and the change in color is not the reason for the decreased efficacy.

2. The method of claim 1, wherein the color of the solution darkens with time to indicate a diminished efficacy based upon freshness of the solution.

3. The method of claim 1, wherein the change in color is caused by oxidation of the beet root powder and other constituents.

4. The method of claim 1, wherein the composition is encapsulated as a powdered mixture in a capsule.

5. The method of claim 1, wherein the composition further comprises one or more of: natural sweeteners, citric acid, sea salt, natural flavors, and natural coloring and at least one of the natural sweeteners, citric acid, sea salt, natural flavors, and natural coloring interact with amino acids in solution to effect the color of the solution.

6. The method of claim 1, wherein the color change is caused by an interaction between the beet root powder and at least one constituent chosen from the following group: zinc amino acid chelate and chromium amino acid chelate.

7. The method of claim 1, further comprising the step of allowing the solution an amount of time to settle to indicate a diminished efficacy.

8. The method of claim 1, further comprising the step of adding a colorant to the solution.

9. The method of claim 8, wherein the colorant comprises a coating that is soluble in the solution.

\* \* \* \* \*